United States Patent
Tyus

[11] Patent Number: 5,662,417
[45] Date of Patent: Sep. 2, 1997

[54] THERMAL STABILITY TESTING APPARATUS

[76] Inventor: Philranzo M. Tyus, 1120 Atlantic Ave., Long Beach, Calif. 90813

[21] Appl. No.: 440,982

[22] Filed: May 15, 1995

[51] Int. Cl.$^6$ .................................................. G01N 25/00
[52] U.S. Cl. ............................ 374/45; 374/57; 165/94
[58] Field of Search .......................... 374/45, 46, 47, 374/49, 50, 54, 53, 57, 179, 208; 165/89, 91, 94

[56] References Cited

U.S. PATENT DOCUMENTS

| | | | |
|---|---|---|---|
| 1,652,525 | 12/1927 | Hahnemann et al. | 374/47 |
| 2,026,137 | 12/1935 | Moor | 374/54 |
| 3,248,927 | 5/1966 | Buehler et al. | 374/45 |
| 3,457,784 | 7/1969 | Butler | 374/54 |
| 3,680,356 | 8/1972 | Felton, Jr. | 374/57 |
| 3,726,125 | 4/1973 | Heyman | 374/57 |
| 4,770,542 | 9/1988 | Takagi et al. | 374/57 |
| 4,858,682 | 8/1989 | Odelstam | 165/94 |
| 4,923,306 | 5/1990 | Fauske | 374/54 |
| 5,062,355 | 11/1991 | Greiwe | 165/89 |
| 5,209,568 | 5/1993 | Buffard et al. | 374/45 |
| 5,341,672 | 8/1994 | Kawanami et al. | 374/45 |

FOREIGN PATENT DOCUMENTS 61-223533  10/1986  Japan .................................. 374/57

*Primary Examiner*—G. Bradley Bennett
*Attorney, Agent, or Firm*—Erik M. Arnhem

[57] ABSTRACT

The thermal stability testing apparatus includes a closed test chamber for containing a sample of material that is to be heated by an electrical heater; weight lost by the sample during the heating operation is a measure of the thermal stability of the material. A motor-operated exhaust fan is provided for removing gaseous products of combustion generated during the sample heating operation.

8 Claims, 1 Drawing Sheet

THERMAL STABILITY TESTING APPARATUS

BACKGROUND AND SUMMARY OF THE INVENTION

This invention relates to an apparatus for measuring the the thermal stability of materials particularly dry organic materials that are subject to degradation when subjected to elevated temperatures. The thermal testing apparatus can be used on a range of different materials, e.g. fabrics, rigid plastic materials, wood materials, and fibrous spun materials.

The apparatus of the present invention comprises a chamber adapted to contain a sample of the material to be tested. An electrical heater is located underneath the chamber for heating the chamber wall and the sample. A vent opening in the chamber wall is connected to an exhaust fan, whereby smoke, vapors and volatile gases generated by the sample heating operation are removed from the chamber.

Ash and solid residue remaining in the chamber after the sample heating operation provide an indication of the thermal stability of the test sample.

The testing operation provides an indication of the sample material's thermal stability, i.e. ability to withstand high temperatures without loss of structural integrity. The term thermal stability, as used by me, defines the resistant power of a certain material to "survive" a rigid test of and then be assigned or labeled with an arbitrary quality number, to educate the consumer of the durability of the material, that he/she is contemplating to purchase. The testing operation may also provide an indirect indication of other characteristics, e.g. tensile strength, compression strength, long-time oxidation resistance, and general durability. In this sense, the invention offers a single test that provides a general indication of overall performance of the tested material.

Further features and advantages of the invention will be apparent from the attached drawing and description of an illustrative embodiment of the invention.

IN THE DRAWING

DESCRIPTION OF A PREFERRED EMBODIMENT OF THE INVENTION

Figure 1:
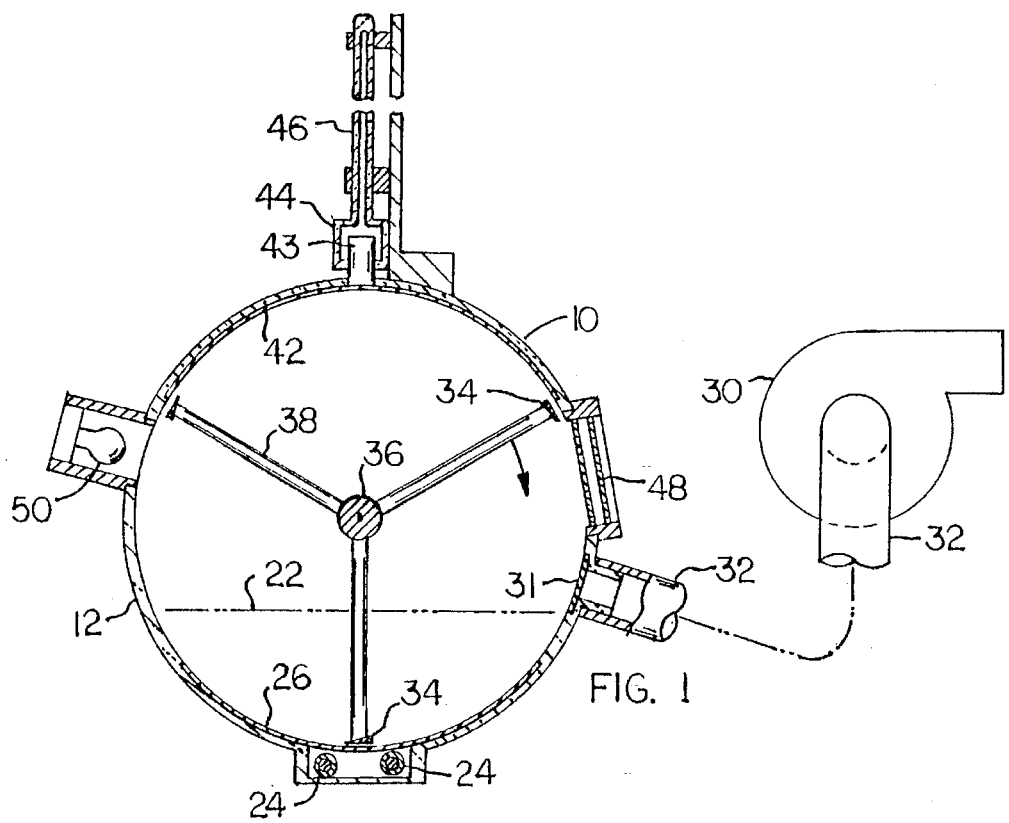
FIG. 1 is a transverse sectional view taken through an apparatus constructed according to the invention.
Figure 2:
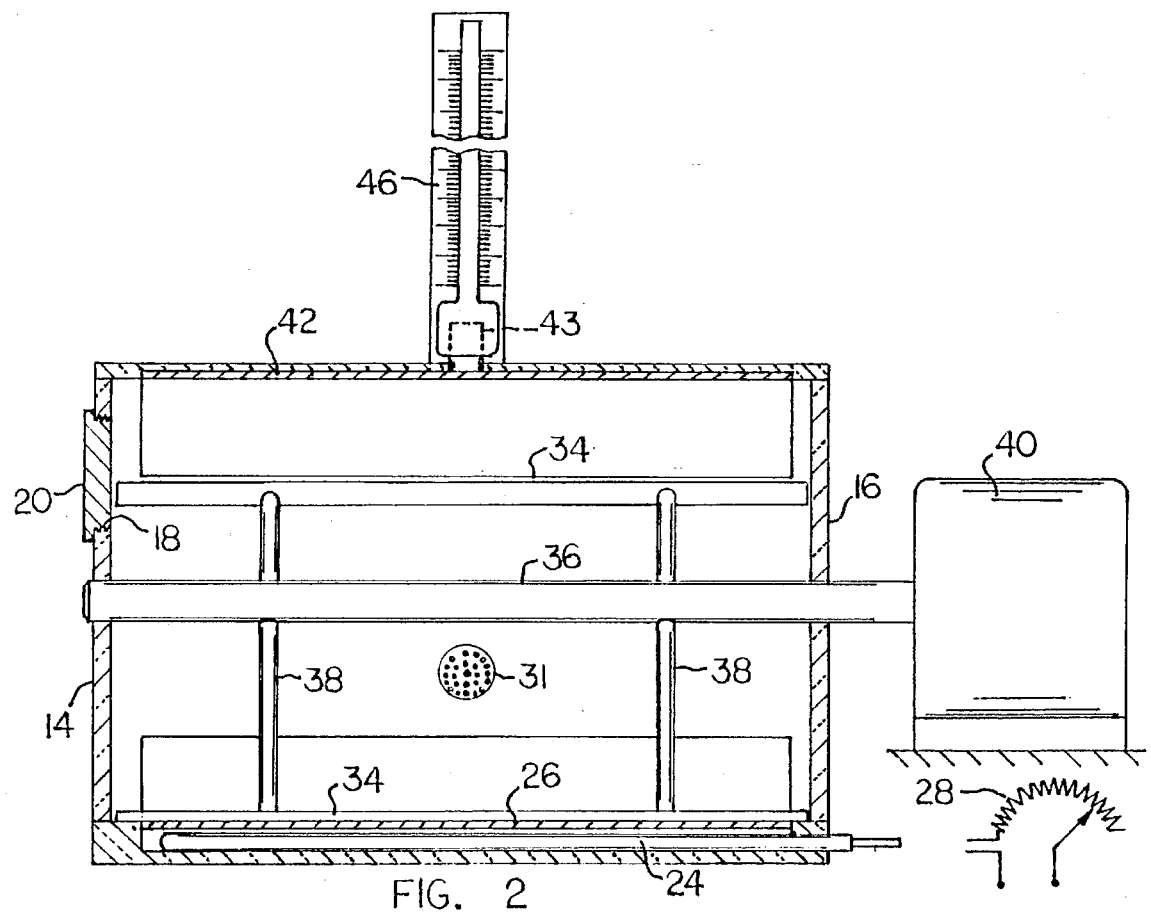
FIG. 2 is a longitudinal sectional view taken through the FIG. 1 apparatus.

The drawings show a testing apparatus that comprises a cylindrical chamber 10 adapted to contain a sample of material that is to be tested for high temperature strength (stability). The cylindrical chamber is defined by a cylindrical tube, or drum, 12 formed out of ceramic or other material that is resistant to elevated temperatures. Ceramic end walls 14 and 16 close opposite ends of the ceramic tube to form a closed chamber for the sample.

The sample, in finely divided form, can be poured or otherwise introduced into the chamber through a port 18 that is normally closed by a screw-on cap 20. The sample material will be cut, sliced or chopped to a granular state prior to being introduced to test chamber 10. In the case of fabrics or flexible sheet materials, the material will be cut into relatively small fragments. The material will be weighed, so that the same mass of comparable materials will be used for each test. Typically, the weight of the test sample will be such as to produce a sample level 22 in the test chamber.

A resistance heater 24 is positioned underneath chamber 10 to supply heat to an arcuate heater plate 26 built into the wall of the test chamber. The heated plate 16 supplies heat to the test sample. Electrical current flow through the heater 24 will be varied by a suitable control means 28, such that comparable materials will be subjected to the same heating action. Different types of materials will require different heating levels.

During the sample heating operation gases and vapors will be generated in the test chamber. A motor-operated exhaust fan 30 is provided for drawing such gases and vapors out of the chamber. As shown in the drawing, the fan is connected to the test chamber by means of a duct 32. A strainer screen 31 is provided in the wall of chamber 10 to prevent the escape of particulates out of the chamber. During the testing operation the test chamber will have a negative pressure.

In order to prevent the sample material from sticking (adhering) to the test chamber surface there is provided a sample scraper means. As shown in the drawing, the scraper means comprises three scraper blades 34 connected to a rotary shaft 36 by spokes 38. An electric motor 40 has a drive connection to the shaft, whereby the shaft is rotated clockwise to move the scraper blades 34 along the chamber 10 surface. The shaft 36 axis may be offset a slight distance downwardly from the chamber axis so that blades 34 have engagement only with the lower half of the chamber circumference. The scraper blades lift material from the chamber surface to prevent the material from sticking to the chamber surface.

The high temperature stability of the test sample material is related to the percentage of the sample that is lost by reason of the heating operation. A relatively small percentage loss indicates good high temperature stability. A relatively large percentage loss indicates poor high temperature stability.

The weight percentage loss can be determined in various ways, e.g. by weighing the sample before and after the heating operation. In the apparatus shown in the drawing, the weight loss is determined by measuring the heat accumulated in the sample by the heating operation.

In order to sense the heat content of the sample there is provided in the roof surface of the test chamber an arcuate radiation-responsive plate 42. Heat is radiated from the heated sample material onto arcuate plate 42, which is thereby heated to a temperature related to the mass of the sample.

The temperature of radiation-sensitive plate 42 can be measured by a thermocouple, using pyrometer technology. As shown in the drawing, the temperature measuring system comprises a conductive rod or pin 43 extending from arcuate plate 42 into the reservoir 44 of a temperature indicating instrument 46. Mercury is heated by the pin to produce an instrument reading related to the temperature of arcuate 42. The instrument 46 will have graduations indicating the thermal stability of various materials tested.

This instrument 46 then determines the temperature by means of a scale graduated into thermal stability units assigned the materials to be tested.

The instrument (46) resembles the conventional thermometer in some respects, in that it is provided, preferably with a glass bulb with the numbered thermal stability scale etched onto it and containing a liquid (mercury or colored alcohol) that is sealed in and rises and falls with changes of temperature.

As an example, the instrument scale may have numbers five or ten, on its right hand side, indicating a five or ten minutes operation, respectively, having the capacity to reach one hour and fifty minutes. On the left hand side of this instrument scale progressive numbers are provided, translating into thermal stability units, to be selected arbitrarily, that will correspond to the time span of a tested material's thermal stability, applied or assigned to the progressive heat treatment in the metamorphic drum.

One will thus be able to establish a quality or a product number, representing the finished product of the same material undergoing the metamorphic process. This quality number will be important to the consumer when purchasing a product.

The operator of the device, according to the invention, must determine by repeated experimentation the selection of thermal stability, depending on the consistancy of the material to be tested, as some material naturally tolerate varying degrees of heat treatment.

It is often desirable to visually study the test sample during the progress of the sample heating operation. Accordingly, the test chamber 10 is equipped with an observation window 48 and light source 50. The light source illuminates the interior of the test chamber so that the human technician can observe the condition of the test sample during the heating operation.

The testing apparatus offers a relatively low cost method for testing a variety of different materials for high temperature stability on a comparison basis. While the drawings necessarily shown a specific apparatus embodying features of the invention, it will be appreciated that the invention can be practiced in various forms and configurations.

What is claimed is:

1. A thermal stability testing apparatus, comprising:

a closed test chamber having an arcuate lower surface and a roof surface;

means for introducing a test sample into the test chamber;

means for applying heat to the arcuate lower surface;

means for scraping the test chamber;

means for venting gaseous products of combustion from the closed test chamber;

a radiation-responsive means on the roof surface of said chamber; and means for measuring the temperature of said radiation-responsive means.

2. The testing apparatus of claim 1, wherein said heat-applying means comprises an arcuate heating plate built into the test chamber so that the heating plate forms part of said arcuate lower surface.

3. The testing apparatus of claim 1, wherein said scraping means comprises a rotary shaft, a plurality of scraper blades equidistantly spaced from said shaft, and spoke means connecting said blades to said shaft.

4. The testing apparatus of claim 3, wherein said scraping means further comprises an electric motor having a drive connection to said shaft whereby the shaft rotates around the shaft axis to move the scraper blades.

5. The testing apparatus of claim 1, wherein said radiation-responsive means comprises an arcuate radiation-responsive plate built into the roof surface of the test chamber.

6. The testing apparatus of claim 1, wherein said venting means comprises a motor-operated exhaust fan.

7. The testing apparatus of claim 6, wherein said venting means further comprises a duct extending between said test chamber and said fan.

8. The testing apparatus of claim 1, wherein said test chamber has a cylindrical configuration.

* * * * *